US005780417A

United States Patent [19]

Gorlin

[11] Patent Number: 5,780,417

[45] Date of Patent: Jul. 14, 1998

[54] LIGHT DUTY LIQUID CLEANING COMPOSITIONS

[75] Inventor: Philip A. Gorlin, Monmouth Junction, N.J.

[73] Assignee: Colgate-Palmolive Company, Piscataway, N.J.

[21] Appl. No.: 904,162

[22] Filed: Jul. 31, 1997

[51] Int. Cl.$^6$ ..... C11D 1/83; A61K 7/50

[52] U.S. Cl. ..... 510/426; 510/218; 510/421; 510/422; 510/424; 510/425; 510/428; 560/198

[58] Field of Search ..... 510/218, 421, 510/422, 424, 425, 426, 428; 560/198

[56] References Cited

U.S. PATENT DOCUMENTS

| | | | |
|---|---|---|---|
| 2,674,619 | 4/1954 | Lundsted | 560/198 |
| 4,784,789 | 11/1988 | Jeschke et al. | 510/394 |
| 5,244,593 | 9/1993 | Roselle et al. | 510/127 |
| 5,417,891 | 5/1995 | Gomes et al. | 510/425 |
| 5,562,912 | 10/1996 | Burke et al. | 424/401 |
| 5,616,548 | 4/1997 | Thomas et al. | 510/242 |

*Primary Examiner*—Paul Lieberman
*Assistant Examiner*—Necholus Ogden
*Attorney, Agent, or Firm*—Richard E. Nanfeldt; James Serafino

[57] ABSTRACT

A light duty liquid detergent with desirable cleansing properties and mildness to the human skin comprising: two sulfonate surfactants, an alkali metal or ammonium salt of a $C_{8-18}$ ethoxylated alkyl ether sulfate anionic surfactant, an alkyl polyglucoside surfactant, an ethoxylated/propoxylated nonionic surfactant and water.

4 Claims, No Drawings

LIGHT DUTY LIQUID CLEANING COMPOSITIONS

FIELD OF INVENTION

This invention relates to a light duty liquid cleaning composition which imparts enhanced mildness to the skin and is designed in particular for dishware and which is effective in removing grease soil and in leaving unrinsed surfaces with a shiny appearance.

BACKGROUND OF THE INVENTION

In recent years all-purpose liquid detergents have become widely accepted for cleaning hard surfaces, e.g., painted woodwork and panels, tiled walls, wash bowls, bathtubs, linoleum or tile floors, washable wall paper, etc. Such all-purpose liquids comprise clear and opaque aqueous mixtures of water-soluble synthetic organic detergents and water-soluble detergent builder salts. In order to achieve comparable cleaning efficiency with granular or powdered all-purpose cleaning compositions, use of water-soluble inorganic phosphate builder salts was favored in the prior art all-purpose liquids. For example, such early phosphate-containing compositions are described in U.S. Pat. Nos. 2,560,839; 3,234,138; 3,350,319; and British Patent No. 1,223,739.

In view of the environmentalist's efforts to reduce phosphate levels in ground water, improved all-purpose liquids containing reduced concentrations of inorganic phosphate builder salts or non-phosphate builder salts have appeared. A particularly useful self-opacified liquid of the latter type is described in U.S. Pat. No. 4,244,840.

However, these prior art all-purpose liquid detergents containing detergent builder salts or other equivalent tend to leave films, spots or streaks on cleaned unrinsed surfaces, particularly shiny surfaces. Thus, such liquids require thorough rinsing of the cleaned surfaces which is a time-consuming chore for the user.

In order to overcome the foregoing disadvantage of the prior art all-purpose liquid, U.S. Pat. No. 4,017,409 teaches that a mixture of paraffin sulfonate and a reduced concentration of inorganic phosphate builder salt should be employed. However, such compositions are not completely acceptable from an environmental point of view based upon the phosphate content. On the other hand, another alternative to achieving phosphate-free all-purpose liquids has been to use a major proportion of a mixture of anionic and nonionic detergents with minor amounts of glycol ether solvent and organic amine as shown in U.S. Pat. No. 3,935,130. Again, this approach has not been completely satisfactory and the high levels of organic detergents necessary to achieve cleaning cause foaming which, in turn, leads to the need for thorough rinsing which has been found to be undesirable to today's consumers.

Another approach to formulating hard surface or all-purpose liquid detergent composition where product homogeneity and clarity are important considerations involves the formation of oil-in-water (o/w) microemulsions which contain one or more surface-active detergent compounds, a water-immiscible solvent (typically a hydrocarbon solvent), water and a "cosurfactant" compound which provides product stability. By definition, an o/w microemulsion is a spontaneously forming colloidal dispersion of "oil" phase particles having a particle size in the range of about 25 to about 800 Å in a continuous aqueous phase.

In view of the extremely fine particle size of the dispersed oil phase particles, microemulsions are transparent to light and are clear and usually highly stable against phase separation.

Patent disclosures relating to use of grease-removal solvents in o/w microemulsions include, for example, European Patent Applications EP 0137615 and EP 0137616—Herbots et al; European Patent Application EP 0160762—Johnston et al; and U.S. Pat. No. 4,561,991—Herbots et al. Each of these patent disclosures also teaches using at least 5% by weight of grease-removal solvent.

It also is known from British Patent Application GB 21 44763A to Herbots et al, published Mar. 13, 1985, that magnesium salts enhance grease-removal performance of organic grease-removal solvents, such as the terpenes, in o/w microemulsion liquid detergent compositions. The compositions of this invention described by Herbots et al. require at least 5% of the mixture of grease-removal solvent and magnesium salt and preferably at least 5% of solvent (which may be a mixture of water-immiscible non-polar solvent with a sparingly soluble slightly polar solvent) and at least 0.1% magnesium salt.

However, since the amount of water immiscible and sparingly soluble components which can be present in an o/w microemulsion, with low total active ingredients without impairing the stability of the microemulsion is rather limited (for example, up to about 18% by weight of the aqueous phase), the presence of such high quantities of grease-removal solvent tend to reduce the total amount of greasy or oily soils which can be taken up by and into the microemulsion without causing phase separation.

The present invention relates to novel light duty liquid detergent compositions with high foaming properties, containing a sulfonate surfactants, an ammonium salt of an ethoxylated alkyl ether sulfate surfactant, a sucroglyceride surfactant, an alkyl polyglucoside surfactant and water.

The prior art is replete with light duty liquid detergent compositions containing nonionic surfactants in combination with anionic and/or betaine surfactants wherein the nonionic detergent is not the major active surfactant, as shown in U.S. Pat. No. 3,658,985 wherein an anionic based shampoo contains a minor amount of a fatty acid alkanolamide. U.S. Pat. No. 3,769,398 discloses a betaine-based shampoo containing minor amounts of nonionic surfactants. This patent states that the low foaming properties of nonionic detergents renders its use in shampoo compositions non-preferred. U.S. Pat. No. 4,329,335 also discloses a shampoo containing a betaine surfactant as the major ingredient and minor amounts of a nonionic surfactant and of a fatty acid mono- or di-ethanolamide. U.S. Pat. No. 4,259,204 discloses a shampoo comprising 0.8–20% by weight of an anionic phosphoric acid ester and one additional surfactant which may be either anionic, amphoteric, or nonionic. U.S. Pat. No. 4,329,334 discloses an anionic-amphoteric based shampoo containing a major amount of anionic surfactant and lesser amounts of a betaine and nonionic surfactants.

U.S. Pat. No. 3,935,129 discloses a liquid cleaning composition based on the alkali metal silicate content and containing five basic ingredients, namely, urea, glycerin, triethanolamine, an anionic detergent and a nonionic detergent. The silicate content determines the amount of anionic and/or nonionic detergent in the liquid cleaning composition. However, the foaming property of these detergent compositions is not discussed therein.

U.S. Pat. No. 4,129,515 discloses a heavy duty liquid detergent for laundering fabrics comprising a mixture of substantially equal amounts of anionic and nonionic surfactants, alkanolamines and magnesium salts, and, optionally, zwitterionic surfactants as suds modifiers.

U.S. Pat. No. 4,224,195 discloses an aqueous detergent composition for laundering socks or stockings comprising a specific group of nonionic detergents, namely, an ethylene oxide of a secondary alcohol, a specific group of anionic detergents, namely, a sulfuric ester salt of an ethylene oxide adduct of a secondary alcohol, and an amphoteric surfactant which may be a betaine, wherein either the anionic or nonionic surfactant may be the major ingredient.

The prior art also discloses detergent compositions containing all nonionic surfactants as shown in U.S. Pat. Nos. 4,154,706 and 4,329,336 wherein the shampoo compositions contain a plurality of particular nonionic surfactants in order to effect desirable foaming and detersive properties despite the fact that nonionic surfactants are usually deficient in such properties.

U.S. Pat. No. 4,013,787 discloses a piperazine based polymer in conditioning and shampoo compositions which may contain all nonionic surfactant or all anionic surfactant.

U.S. Pat. No. 4,671,895 teaches a liquid detergent composition containing an alcohol sulfate surfactant, a nonionic surfactant, a paraffin sulfonate surfactant, an alkyl ether sulfate surfactant and water.

U.S. Pat. No. 4,450,091 discloses high viscosity shampoo compositions containing a blend of an amphoteric betaine surfactant, a polyoxybutylene polyoxyethylene nonionic detergent, an anionic surfactant, a fatty acid alkanolamide and a polyoxyalkylene glycol fatty ester. But, none of the exemplified compositions contains an active ingredient mixture wherein the nonionic detergent is present in major proportion, probably due to the low foaming properties of the polyoxybutylene polyoxyethylene nonionic detergent.

U.S. Pat. No. 4,595,526 describes a composition comprising a nonionic surfactant, a betaine surfactant, an anionic surfactant and a $C_{12}$–$C_{14}$ fatty acid monoethanolamide foam stabilizer.

U.S. Pat. Nos. 4,675,422; 4,698,181; 4,724,174; 4,770,815 and 4,921,942 disclose alkyl succinamates but the compositions are non related to light duty liquid compositions.

However, none of the above-cited patents discloses a liquid detergent composition containing two sulfonate surfactants, an alkali metal or ammonium salt of an ethoxylated alkyl ether sulfate surfactant, an alkyl polyglucoside surfactant, an ethoxylated/propoxylated nonionic surfactant and water, wherein the composition does not contain any low molecular weight mono- or di-glucoside, abrasives, silicas, alkaline earth metal carbonates, alkyl glycine surfactant, cyclic imidinium surfactant, alkali metal carbonates or more than 3 wt. % of a fatty acid or its salt thereof, wherein the composition does not contain a nonionic made from a fatty alcohol and only ethylene oxide and the composition does not contain alkanol amides, amine oxide surfactant, betaine surfactant, glycol ether cosurfactants or more than 0.3 wt. % of a water insoluble hydrocarbon such as a perfume.

SUMMARY OF THE INVENTION

It has now been found that a light duty liquid composition which has desirable cleaning properties together with enhanced mildness to the human skin.

An object of this invention is to provide a novel light duty liquid detergent composition containing a sulfonate surfactant, an alkali metal salt or ammonium salt of an ethoxylated alkyl ether sulfate surfactant, an alkyl polyglucoside surfactant, an amine oxide surfactant, an ethoxylated monoalkanol amide, a monoalkanol amide and water wherein the composition does not contain any silicas, abrasives, alkali metal carbonates, alkaline earth metal carbonates, alkyl glycine surfactant, cyclic imidinium surfactant, low molecular weight mono- or di-glucoside organoaluminum containing compounds, organo titanium containing compounds, triethylene tetramine hexaacetic acid, imidazolenes, or more than 3 wt. % of a fatty acid or salt thereof, wherein the composition does not contain a nonionic made from a fatty alcohol and only ethylene oxide and the composition does not contain alkanol amides, amine oxide surfactant, betaine surfactant, glycol ether cosurfactants or more than 0.3 wt. % of a water insoluble hydrocarbon such as a perfume.

Another object of this invention is to provide a novel light duty liquid detergent with desirable high foaming and cleaning properties which is very mild to the human skin.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

DETAILED DESCRIPTION OF THE INVENTION

The light duty liquid compositions of the instant invention comprise approximately by weight:

(a) 5% to 15% of an alkali metal salt or ammonium salt of a $C_{8-18}$ ethoxylated alkyl ether sulfate;

(b) 1% to 20% of a alkali metal salt of a sulfonate surfactant;

(c) 5% to 15% of an alkaline earth metal salt of a sulfonate surfactant;

(d) 0.1% to 6% of an ethoxylated/propoxylated nonionic surfactant;

(e) 8% to 20% of an alkyl polyglucoside surfactant; and (f) the balance being water, wherein the composition does not contain a nonionic made from a fatty alcohol and only ethylene oxide and the composition does not contain alkanol amides, amine oxide surfactant, betaine surfactant, glycol ether cosurfactants or more than 0.3 wt. % of a water insoluble hydrocarbon such as a perfume.

The $C_{8-18}$ ethoxylated alkyl ether sulfate surfactants used in the instant composition have the structure $$R-(OCHCH_2)_nOSO_3^{-M+}$$

wherein n is about 1 to about 22 more preferably 1 to 3 and R is an alkyl group having about 8 to about 18 carbon atoms, more preferably 12 to 15 and natural cuts, for example, $C_{12-14}$; $C_{12-15}$ and M is an ammonium cation or an alkali metal cation, most preferably sodium or ammonium. The ethoxylated alkyl ether sulfate is present in the composition at a concentration of about 5 wt. % to about 13 wt. %, more preferably about7 wt. % to 12 wt. %.

The ethoxylated alkyl ether sulfate may be made by sulfating the condensation product of ethylene oxide and $C_{8-10}$ alkanol, and neutralizing the resultant product. The ethoxylated alkyl ether sulfates differ from one another in the number of carbon atoms in the alcohols and in the number of moles of ethylene oxide reacted with one mole of such alcohol. Preferred ethoxylated alkyl ether polyethenoxy sulfates contain 12 to 15 carbon atoms in the alcohols and in the alkyl groups thereof, e.g., sodium myristyl (3 EO) sulfate.

Ethoxylated $C_{8-18}$ alkylphenyl ether sulfates containing from 2 to 6 moles of ethylene oxide in the molecule are also suitable for use in the invention compositions. These detergents can be prepared by reacting an alkyl phenol with 2 to 6 moles of ethylene oxide and sulfating and neutralizing the resultant ethoxylated alkylphenol.

The linear alkyl benzene sulfonate contains from 10 to 16 carbon atoms in the alkyl group are used in the instant compositions wherein the alkyl benzene sulfonates has a high content of 3- (or higher) phenyl isomers and a correspondingly low content (well below 50%) of 2- (or lower) phenyl isomers, that is, wherein the benzene ring is preferably attached in large part at the 3 or higher (for example, 4, 5, 6 or 7) position of the alkyl group and the content of the isomers in which the benzene ring is attached in the 2 or 1 position.

One of the sulfonate surfactants is an alkali metal salt of a $C_{10}$–$C_{16}$ linear alkyl benzene sulfonate or a $C_{10}$–$C_{16}$ paraffin sulfonate used at a concentration of about 1 wt. % to about 20 wt. %, more preferably about 3 wt. % to about 1.5 wt. % in the instant compositions.

The other sulfonate surfactant is an alkaline earth metal salt of a $C_{10}$–$C_{16}$ linear alkyl benzene sulfonate or a $C_{10}$–$C_{16}$ paraffin sulfonate used at a concentration of 5 wt. % to 15 wt. %, more preferably 7 wt. % to 11 wt. % in the instant compositions.

The instant compositions contain about 3 wt. % to about 20 wt. %, more preferably 4 wt. % to 18 wt. % of an alkyl polysaccharide surfactant. The alkyl polysaccharides surfactants, which are used in conjunction with the aforementioned surfactant have a hydrophobic group containing from about 8 to about 20 carbon atoms, preferably from about 10 to about 16 carbon atoms, most preferably from about 12 to about 14 carbon atoms, and polysaccharide hydrophilic group containing from about 1.5 to about 10, preferably from about 1.5 to about 4, most preferably from about 1.6 to about 2.7 saccharide units (e.g., galactoside, glucoside, fructoside, glucosyl, fructosyl; and/or galactosyl units). Mixtures of saccharide moieties may be usedin the alkyl polysaccharide surfactants. The number x indicates the number of saccharide units in a particular alkyl polysaccharide surfactant. For a particular alkyl polysaccharide molecule x can only assume integral values. In any physical sample of alkyl polysaccharide surfactants there will be in general molecules having different x values. The physical sample can be characterized by the average value of x and this average value can assume non-integral values. In this specification the values of x are to be understood to be average values. The hydrophobic group (R) can be attached at the 2-, 3-, or 4- positions rather than at the 1-position, (thus giving e.g. a glucosyl or galactosyl as opposed to a glucoside or galactoside). However, attachment through the 1- position, i.e., glucosides, galactoside, fructosides, etc., is preferred. In the preferred product the additional saccharide units are predominately attached to the previous saccharide unit's 2-position. Attachment through the 3-, 4-, and 6-positions can also occur. Optionally and less desirably there can be a polyalkoxide chain joining the hydrophobic moiety (R) and the polysaccharide chain. The preferred alkoxide moiety is ethoxide.

Typical hydrophobic groups include alkyl groups, either saturated or unsaturated, branched or unbranched containing from about 8 to about 20, preferably from about 10 to about 18 carbon atoms. Preferably, the alkyl group is a straight chain saturated alkyl group. The alkyl group can contain up to 3 hydroxy groups and/or the polyalkoxide chain can contain up to about 30, preferably less than about 10, alkoxide moieties.

Suitable alkyl polysaccharides are decyl, dodecyl, tetradecyl, pentadecyl, hexadecyl, and octadecyl, di-, tri-, tetra-, penta-, and hexaglucosides, galactosides, lactosides, fructosides, fructosyls, lactosyls, glucosyls and/or galactosyls and mixtures thereof.

The alkyl monosaccharides are relatively less soluble in water than the higher alkyl polysaccharides. When used in admixture with alkyl polysaccharides, the alkyl monosaccharides are solubilized to some extent. The use of alkyl monosaccharides in admixture with alkyl polysaccharides is a preferred mode of carrying out the invention. Suitable mixtures include coconut alkyl, di-, tri-, tetra-, and pentaglucosides and tallow alkyl tetra-, penta-, and hexaglucosides.

The preferred alkyl polysaccharides are alkyl polyglucosides having the formula $$RO(C_nH_{2n}O)_r(Z)_x$$

wherein Z is derived from glucose, R is a hydrophobic group selected from the group consisting of alkyl, alkylphenyl, hydroxyalkylphenyl, and mixtures thereof in which said alkyl groups contain from about 10 to about 18, preferably from about 12 to about 14 carbon atoms; n is 2 or 3 preferably 2, r is from 0 to 10, preferably 0; and x is from 1.5 to 8, preferably from 1.5 to 4, most preferably from 1.6 to 2.7. To prepare these compounds a long chain alcohol ($R_2OH$) can be reacted with glucose, in the presence of an acid catalyst to form the desired glucoside. Alternatively the alkyl polyglucosides can be prepared by a two step procedure in which a short chain alcohol ($R_1OH$) can be reacted with glucose, in the presence of an acid catalyst to form the desired glucoside. Alternatively the alkyl polyglucosides can be prepared by a two step procedure in which a short chain alcohol ($C_{1-6}$) is reacted with glucose or a polyglucoside (x=2 to 4) to yield a short chain alkyl glucoside (x=1 to 4) which can in turn be reacted with a longer chain alcohol ($R_2OH$) to displace the short chain alcohol and obtain the desired alkyl polyglucoside. If this two step procedure is used, the short chain alkylglucoside content of the final alkyl polyglucoside material should be less than 50%, preferably less than 10%, more preferably less than about 5%, most preferably 0% of the alkyl polyglucoside.

The amount of unreacted alcohol (the free fatty alcohol content) in the desired alkyl polysaccharide surfactant is preferably less than about 2%, more preferably less than about 0.5% by weight of the total of the alkyl polysaccharide. For some uses it is desirable to have the alkyl monosaccharide content less than about 10%.

The used herein, "alkyl polysaccharide surfactant" is intended to represent both the preferred glucose and galactose derived surfactants and the less preferred alkyl polysaccharide surfactants. Throughout this specification, "alkyl polyglucoside" is used to include alkyl polyglycosides because the stereochemistry of the saccharide moiety is changed during the preparation reaction.

An especially preferred APG glycoside surfactant is APG 625 glycoside manufactured by the Henkel Corporation of Ambler, Pa. APG25 is a nonionic alkyl polyglycoside characterized by the formula:

$$C_nH_{2n+1}O(C_6H_{10}O_5)_xH$$

wherein n=10 (2%); n=12 (65%); n=14 (21–28%); n=16 (4–8%) and n=18 (0.5%) and x (degree of polymerization)=1.6. APG 625 has: a pH of 6 to 10 (10% of APG 625 in distilled water); a specific gravity at 25° C. of 1.1 g/ml; a density at 25° C. of 9.1 lbs/gallon; a calculated HLB of 12.1 and a Brookfield viscosity at 35° C., 21 spindle, 5–10 RPM of 3,000 to 7,000 cps.

The polymeric surfactants are block copolymers of ethylene oxide and propylene oxide used in the instant composition at a concentration of about 0.1 wt. % to about 6.0 wt. %, more preferably 0.2 wt. % to 5.0 wt. % and have the following structure:

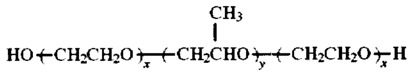

wherein x=about 90 to about 150 and y=about 15 to about 65 and the HLB is about 20 to about 40.

A preferred polymeric surfactant is Pluronic F108, wherein x=127.5 and y=48 with a molecular weight of 14600 and an HLB of 27.

The instant compositions contain about 0 wt. % to about 12 wt. %, more preferably about 1 wt. % to about 10 wt. %, of at least one solubilizing agent which can be sodium xylene sulfonate, sodium cumene sulfonate, a $C_{2-3}$ mono or dihydroxy alkanols such as ethanol, isopropanol and propylene glycol and mixtures thereof. The solubilizing agents are included in order to control low temperature cloud clear properties. Urea can be optionally employed in the instant composition as a supplemental solubilizing agent at a concentration of 0 to about 10 wt. %, more preferably about 0.5 wt. % to about 8 wt. %.

In final form, the instant compositions exhibit stability at reduced and increased temperatures. More specifically, such compositions remain clear and stable in the range of 5° C. to 50° C., especially 10° C. to 43° C. The instant compositions have a light transmission of at least 95%. Such compositions exhibit a pH of 5 to 8. The liquid compositions are readily pourable and exhibit a viscosity in the range of 100 to 600 cps as measured at 25° C. with a Brookfield RVT Viscometer using a #21 spindle rotating at 20 RPM. Preferably, the viscosity is maintained in the range of 300 to 500 cps. The instant compositions have a minimum foam height of 110 mls after 55 rotation at 40° C. as measured by the foam volume test using 0.75 grams of the composition per liter of water and 1 gram of corn oil per liter of water having a hardness of 300 ppm.

The following examples illustrate liquid cleaning compositions of the described invention. Unless otherwise specified, all percentages are by weight. The exemplified compositions are illustrative only and do not limit the scope of the invention. Unless otherwise specified, the proportions in the examples and elsewhere in the specification are by weight.

EXAMPLE 1

The following composition in wt. % was prepared by simple mixing procedure at 25° C.:

| | A | B |
|---|---|---|
| Sodium salt of a $C_{10}$–$C_{16}$ linear alkyl benzene sulfonate | 3 | 15 |
| Magnesium salt of a $C_{10}$–$C_{16}$ linear alkyl benzene sulfonate | 9 | |
| APG625 | 10 | 10 |
| NaAEOS (1.3EO) | 11.6 | 8.5 |
| Pluronic 108 | 2 | 2 |
| Water | Bal. | Bal. |
| Initial Foam Volume (ml) | | |
| Shell Foam % FPR | | |
| Baumgartner Lard Test | 21.1 | 25.5 |

What is claimed:

1. A clear light duty liquid cleaning composition which consisting of approximately by weight:

(a) 5% to 15% of an alkali metal or ammonium salt of a $C_{8-18}$ ethoxylated alkyl ether sulfate;

(b) 5% to 15% of an alkaline earth metal salt of a sulfonate surfactant selected from the group consisting of $C_{10-16}$ alkyl benzene sulfonate and/or $C_{10-16}$ paraffin sulfonate surfactant;

(c) 1% to 20% of an alkali metal salt of a sulfonate surfactant selected from the group consisting of $C_{10-16}$ alkyl benzene sulfonate and/or $C_{10-16}$ paraffin sulfonate surfactant;

(d) 3% to 20% of an alkyl polyglucoside surfactant;

(e) 0.1% to 6% of an ethoxylated/propoxylated nonionic polymeric surfactant wherein the ethoxylated/propoxylated nonionic polymer surfactant has the structure:

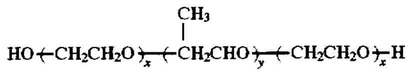

wherein x equals about 90 to about 150 and y equals about 15 to about 65; and (f) the balance being water, wherein said composition does not contain a nonionic surfactant containing a fatty alcohol or an alkanol amide.

2. The composition of claim 1, further including a solubilizing agent which is a $C_{2-3}$ mono or dihydroxy alkanol.

3. The composition of claim 1, further including a solubilizing agent which is selected from the group consisting of isopropanol, ethanol and propylene glycol and mixtures thereof.

4. The composition of claim 1, further including a solubilizing agent which is sodium xylene sulfonate or sodium cumene sulfonate.

* * * * *